United States Patent
James

(10) Patent No.: US 12,221,628 B2
(45) Date of Patent: Feb. 11, 2025

(54) PARTIONING OF ADULT MESENCHYMAL STEM CELLS

(71) Applicant: The Johns Hopkins University, Baltimore, MD (US)

(72) Inventor: Aaron James, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 880 days.

(21) Appl. No.: 17/287,810

(22) PCT Filed: Oct. 23, 2019

(86) PCT No.: PCT/US2019/057610
§ 371 (c)(1),
(2) Date: Apr. 22, 2021

(87) PCT Pub. No.: WO2020/086687
PCT Pub. Date: Apr. 30, 2020

(65) Prior Publication Data
US 2021/0395685 A1    Dec. 23, 2021

Related U.S. Application Data

(60) Provisional application No. 62/749,154, filed on Oct. 23, 2018.

(51) Int. Cl.
*C12N 5/077* (2010.01)
*A61K 35/28* (2015.01)

(52) U.S. Cl.
CPC ............ *C12N 5/0653* (2013.01); *A61K 35/28* (2013.01); *C12N 2506/1384* (2013.01)

(58) Field of Classification Search
CPC .......... C12N 5/0653; C12N 2506/1384; A61K 35/28
See application file for complete search history.

(56) References Cited

U.S. PATENT DOCUMENTS

2012/0177618 A1* 7/2012 Parekkadan ........... A61K 35/28
                                                   435/372
2019/0269739 A1* 9/2019 Brodie .................... A61P 35/00
2019/0314417 A1* 10/2019 Wobma ................ C12N 5/0663

FOREIGN PATENT DOCUMENTS

WO    1996023059 A1    8/1996

OTHER PUBLICATIONS

Galland S, Vuille J, Martin P, Letovanec I, Caignard A, Fregni G, Stamenkovic I. Tumor-Derived Mesenchymal Stem Cells Use Distinct Mechanisms to Block the Activity of Natural Killer Cell Subsets. Cell Rep. Sep. 19, 2017;20(12):2891-2905. doi: 10.1016/j.celrep.2017.08.089. PMID: 28930684. (Year: 2017).*
Nicodemou et al., "Mesenchymal Stromal/Stem Cell Separation Methods: Concise Review." Cell Tissue Bank, 18 (4):443-460, 2017.
Frizzera et al., "Treatment of Peri-Implant Soft Tissue Defects: A Narrative Review," Braz Oral Res, vol. 33, pp. 1-7, 2019.
International Search Report and the Written Opinion from PCT Application No. PCT/US2019/057610, dated Jan. 30, 2020, 6 pages.

* cited by examiner

*Primary Examiner* — Maria G Leavitt
*Assistant Examiner* — Joel D Levin
(74) *Attorney, Agent, or Firm* — Fox Rothschild LLP

(57) ABSTRACT

The present invention has developed methods and compositions utilizing the cell surface CD107a (LAMP-1) as a marker that divides bone-forming and fat-forming progenitor/stem cells within human adipose tissue. The present invention is able to partition stromal progenitors for improved bone and soft tissue engineering and therapies.

5 Claims, 17 Drawing Sheets

Specification includes a Sequence Listing.

FIGURE 1

Summary of CD107a$^{high}$ cell isolation

| Date | Sample | Frequency (CD107a$^{hi}$CD31$^-$CD45$^-$) | Frequency (CD107a$^{low}$CD31$^-$CD45$^-$) |
|---|---|---|---|
| 6/17/17 | Human Adipose | 43.4% | 25.3% |
| 6/15/17 | Human Adipose | 2.4% | 0.5% |
| 7/20/17 | Human Adipose | 3.78% | 40.53% |
| 8/16/17 | Human Adipose | 7.92% | 38.16% |
| 8/06/18 | Human Adipose | 4.3% | 35% |
| 9/11/18 | Human Adipose | 21.27% | 25.66% |

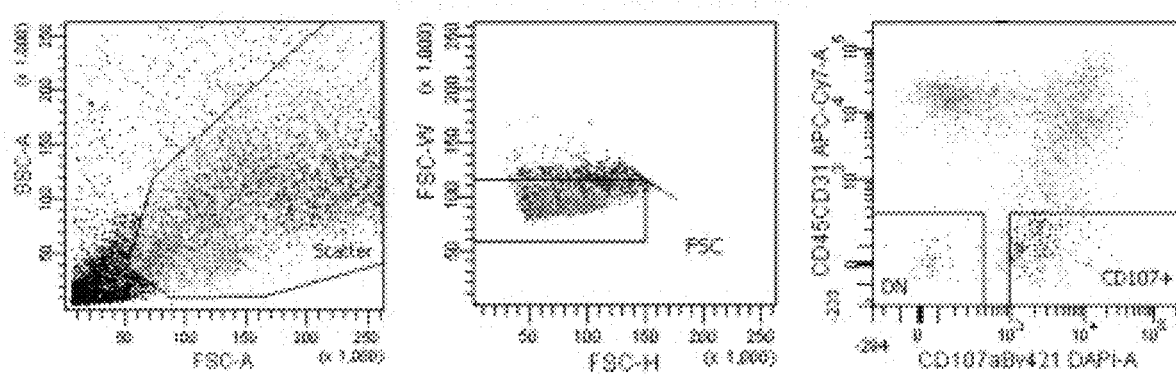

FIGURE 4 Sort on 7-20-17 on MoFlo
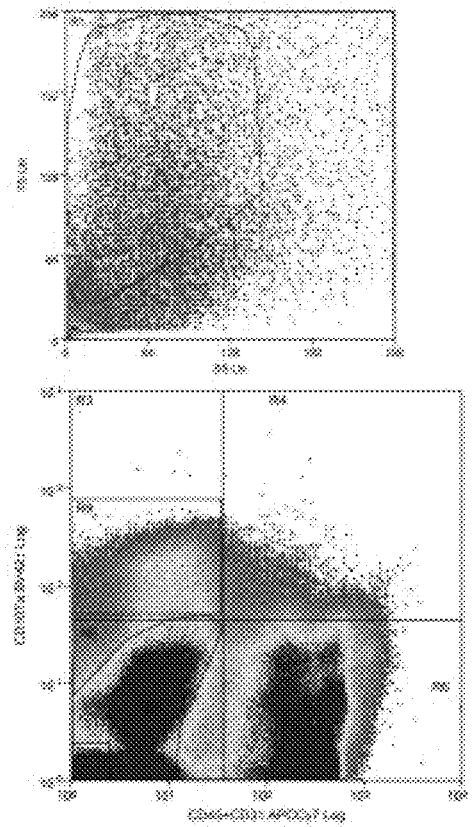
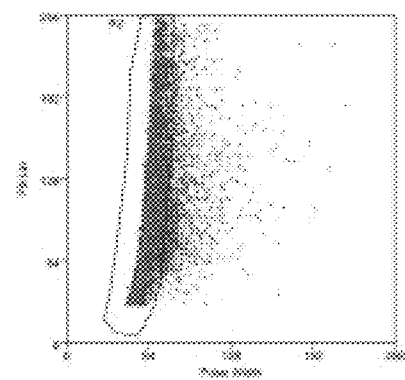

FIGURE 5
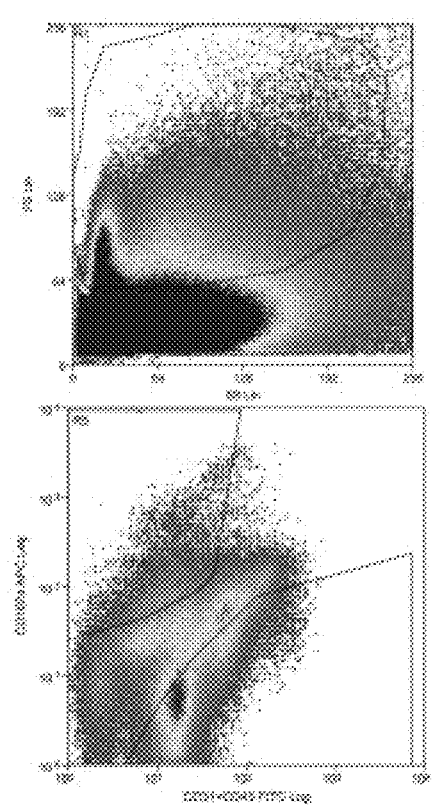
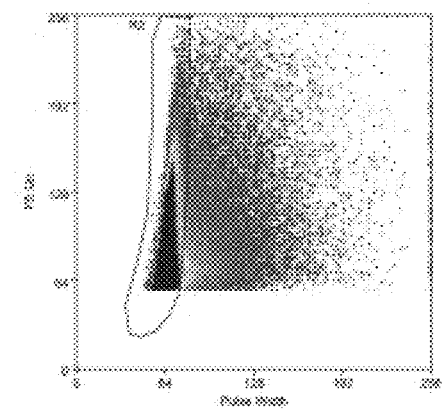

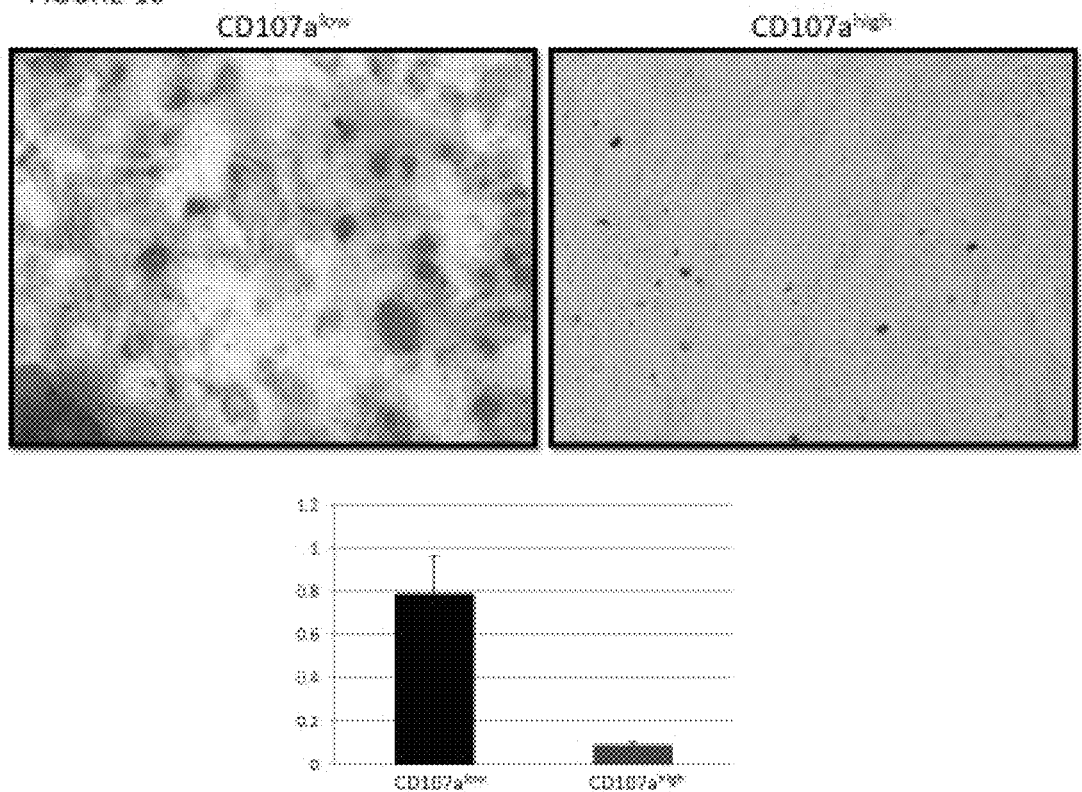

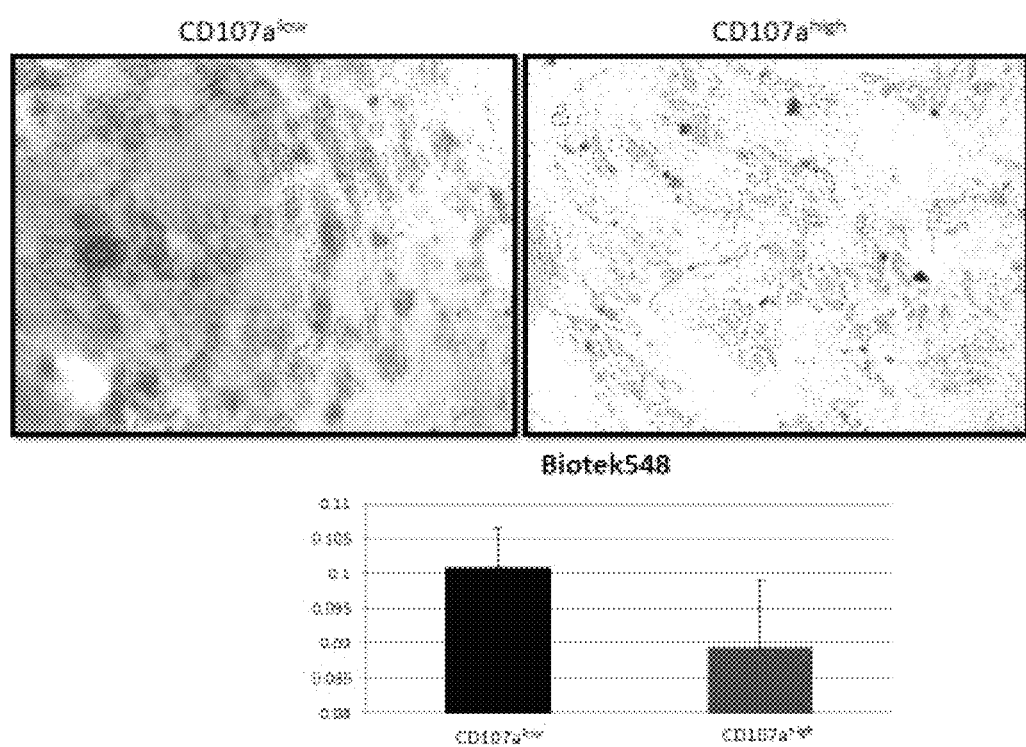
FIGURE 11 CD107a Osteogenic of huASC002

FIGURE 12  CD107a Osteogenic of huASC003
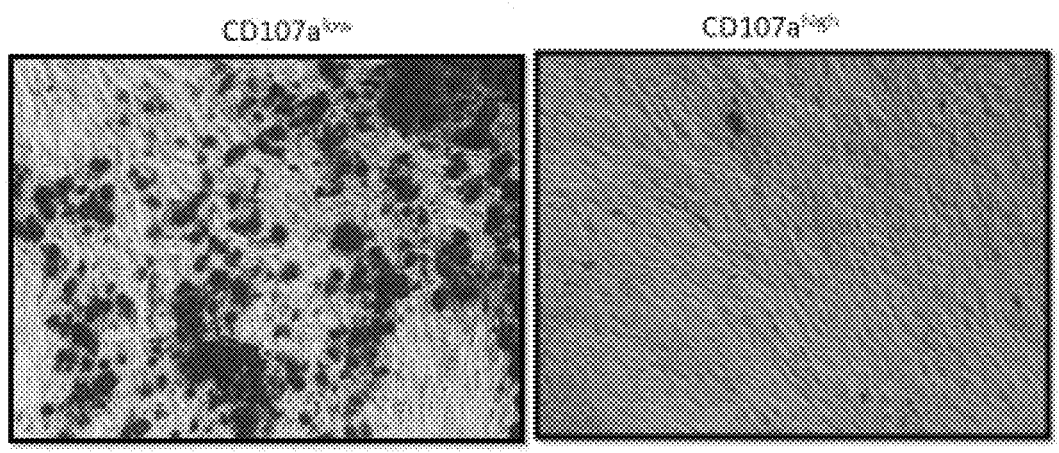
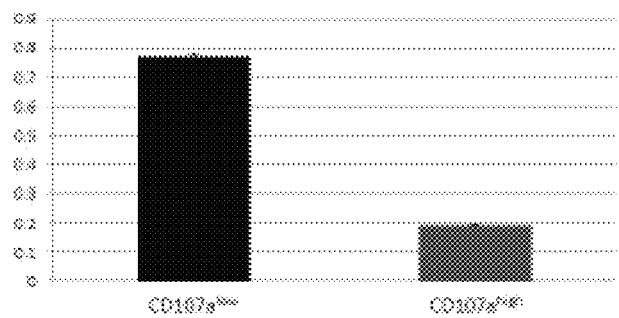
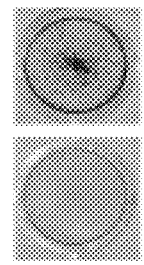

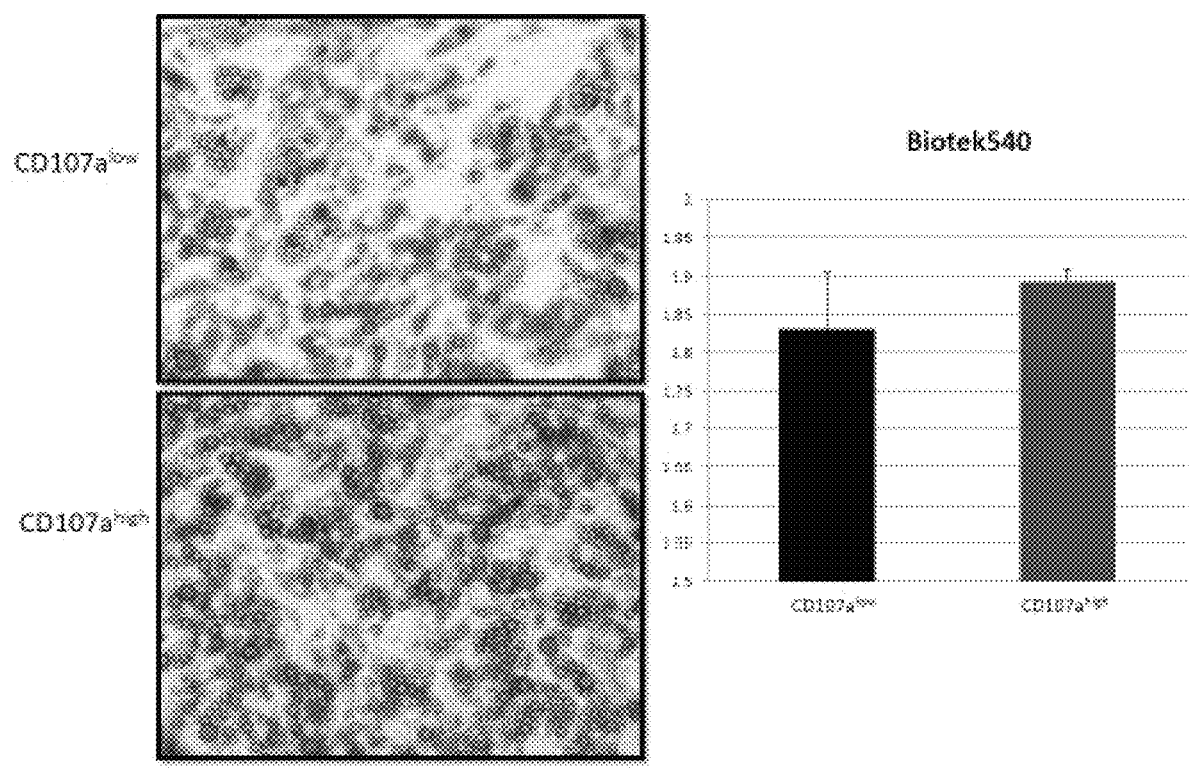

FIGURE 15   CD107a Adipogenic ---huASC002
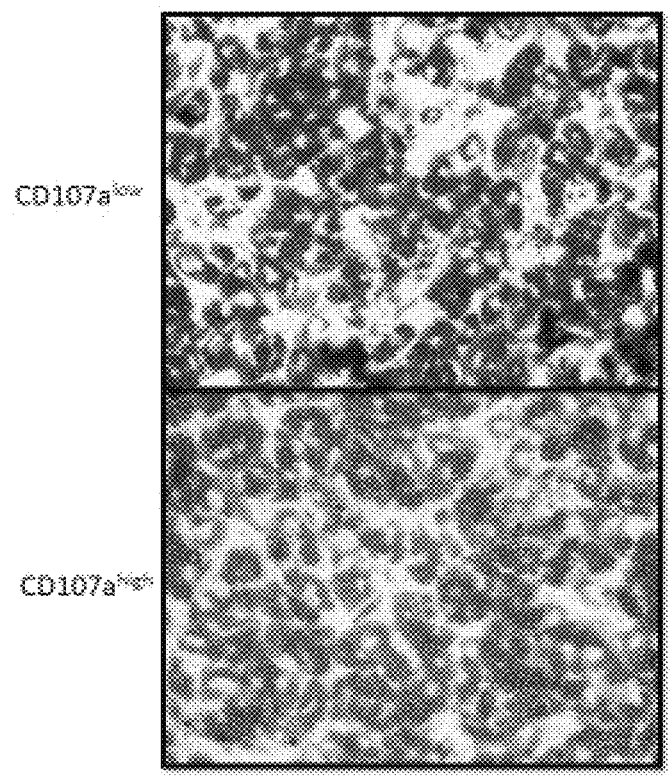
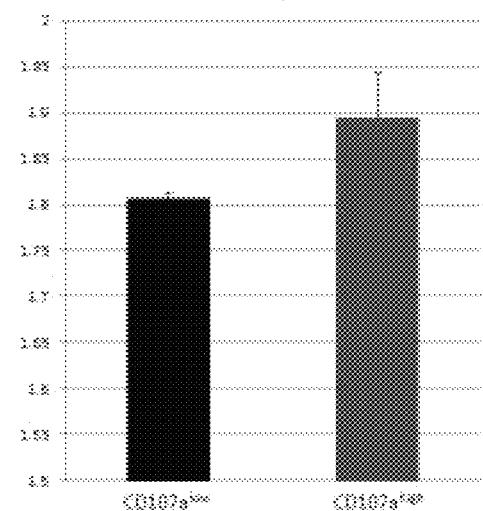

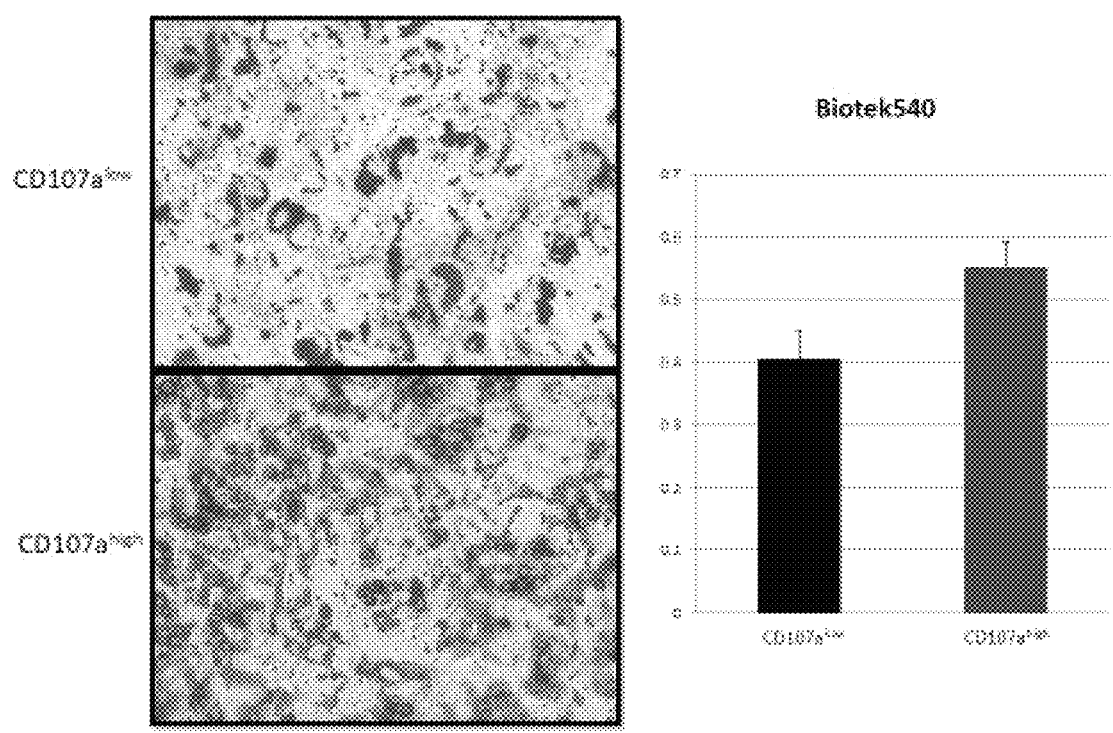

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctggaacggt gaaggtgaca                                                   20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacccttgac ccccacaat                                                    19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
tggacaagaa cagcaacgag ta					22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taccccactc agcccagtgt					20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgagaggat gataaactgg tgg					23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttgcagagag aggactcgga					20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgagagccc tcacactcct c					21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctcctaggc atcacctgtg					20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 gggtgatgt gtttgaactt g                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggcgggta acgatgaaaa t                                          21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagggacttc ctgtaacaat gca                                        23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctcgtactg catgtcccct                                            20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
attgtcactg gtcagctcca g                                          21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accagacatg cctcttgtcc tt                                         22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
gcgaacttca gtccaggtca ac                                              22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagttgcac ctgtatgcct                                                 20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccgtagaag cgccgatagg c                                               21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccacactatc acctcggcc                                                  19

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacaggaaag acaacagaca aatc                                            24

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acggcgggga agactgtgc                                                  19
```

PARTIONING OF ADULT MESENCHYMAL STEM CELLS

CROSS-REFERENCE TO RELATED APPLICATIONS

This application is a National Stage Application filed under 35 U.S.C. § 371, of International Patent Application No PCT/US2019/057610, filed on Oct. 23, 2019, which claims the benefit of and priority to U.S. Provisional Application No. 62/749,154, filed on Oct. 23, 2018. The entire contents of each of these application are incorporated herein by reference in their entirety.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Oct. 23, 2019, is named 048317-630N01US_SL.txt and is 4,762 bytes in size.

BACKGROUND OF THE INVENTION

Autologous stem cell therapies hold great promise for the treatment of defects of bone and soft tissue. Bone defects are common and devastating conditions that are addressed in over 2.2 million surgeries yearly, with estimated annual costs of $56 billion. With an expanding elderly population, total costs for the treatment of bone defect pathologies are expected to balloon. An improved osteoprogenitor cell therapy has numerous potential clinical applications, including non-healing bone defects, fibrous non-unions, and failed integration of orthopedics hardware. With clinical trials of mesenchymal stem cells (MSC)-based bone repair demonstrating suboptimal results, use of a defined progenitor cell is of paramount importance in the field.

The biomedical burden of soft tissue defects is likewise enormous, estimated to be addressed in 5.2 million surgeries yearly. Autologous solutions using rotational or free flaps are technically demanding procedures, with potential for ischemic failure, extended requirements for ICU monitoring, and complications of donor site morbidity. Numerous synthetic and biologic fillers are available, but have wide ranging detractions including leakage, volume loss, foreign body reaction, and fibrosis. An adipoprogenitor cell therapy has many potential applications, including soft tissue defects from traumatic, oncologic, or congenital etiologies, as well as non-healing ulcers, muscle and fat wasting diseases, and even in addressing issues of cosmesis associated with aging.

SUMMARY OF THE INVENTION

The present invention has developed methods and compositions utilizing the cell surface CD107a (LAMP-1) as a marker that divides bone-forming and fat-forming progenitor/stem cells within human mesenchymal tissues. The present invention is able to partition stromal progenitors for improved bone and soft tissue engineering and therapies.

One embodiment of the present invention is a method of separating CD107a mesenchymal stem cells from CD107a$^{low}$ mesenchymal cells. The method comprises the steps of providing mesenchymal stems cells from adipose tissue or other mesenchymal tissues; mixing labeled anti-CD107a with the mesenchymal stem cells; and sorting the cells into a population of CD107a$^{high}$ mesenchymal stem cells and a population of CD107a$^{low}$ mesenchymal stem cells. The CD107a$^{high}$/a$^{low}$ mesenchymal stem cells may have additional marker characteristics such as the cells being CD45$^{+}$CD31$^{-}$, as an example. A population of CD107a$^{high}$ mesenchymal stem cells and a population of CD107a$^{low}$ mesenchymal stem cells of the present invention have been observed to remain undifferentiated when grown under basal cell culture conditions, an example of one method of culturing CD107a$^{high}$/a$^{low}$ mesenchymal stem cell populations. For purposes of clarity, the CD107a$^{high}$/a$^{low}$ mesenchymal stem cells of the present invention are undifferentiated cells that can further be differentiated into specific cell types. A population of CD107a$^{high}$ mesenchymal stem cells of the present invention is greater than 45%, 50%, 55%, 60%, 65%, 70%, 75%, 80%, 85%, 90%, or 95%, CD107a$^{high}$ mesenchymal stem cells. A population of CD107a$^{low}$ mesenchymal stem cells is greater than 45% 50%, 55%, 60%, 65%, 70%, 75%, 80%, 85%, 90%, or 95%, CD107a$^{low}$ mesenchymal stem cells.

Another embodiment of the present invention is a method of differentiating a population of CD107a$^{low}$ mesenchymal stem cells comprising the steps of providing a population of CD107a$^{low}$ mesenchymal stem cells; differentiating the population of CD107a$^{low}$ mesenchymal stem cells; and forming CD107a$^{low}$ osteogenic cells. A population of CD107a$^{low}$ mesenchymal stem cells is differentiated under suitable conditions such as osteogenic differentiation conditions, including addition of ascorbic acid, beta glycerophosphate, in the presence or absence of dexamethasone, as one example. The CD107a$^{low}$ osteogenic cells have increased alkaline phosphatase enzymatic activity and bone nodule deposition when compared to a population of CD107a$^{high}$ mesenchymal stem cells of the present invention. The CD107a$^{low}$ osteogenic cells of the present invention have increased osteoblast specific gene expression compared to the undifferentiated CD107a$^{low}$ mesenchymal stem cells or the CD107a$^{high}$ mesenchymal stem cells of the present invention. By increased is meant the CD107a$^{low}$ osteogenic cells of the present invention have 2×, 3×, 4×, 5× or more of the osteoblast specific gene expression, alkaline phosphatase activity, or alizarin red quantification of bone nodules compare to CD107a$^{high}$ mesenchymal stem cells of the present invention.

Another embodiment of the present invention is a method of differentiating a population of CD107a$^{high}$ mesenchymal stem cells comprising the steps of: providing a population of CD107a$^{high}$ mesenchymal stem cells; differentiating the CD107a$^{high}$ mesenchymal stem cells; and forming adipogenic cells. A population of CD107a$^{high}$ mesenchymal stem cells of the present invention were differentiated under adipogenic differentiation conditions. Such adipogenic differentiation conditions include addition of insulin, dexamethasone, methylxanthine and indomethacin, as one example. The CD107a$^{high}$ adipogenic cells of the present invention have been shown to have increased lipid accumulation by Oil red O staining and quantification, and increased adipocyte specific gene expression. By increased is meant the CD107a$^{high}$ adipogenic cells of the present invention have 2×, 3×, 4×, 5×, or more of the Oil red O staining or adipocyte specific gene as compared to CD107a$^{high}$ mesenchymal stem cells of the present invention.

Another embodiment of the present invention is a population of cells comprising CD107a$^{high}$ mesenchymal stem cells. As stated above, a population of CD107a$^{high}$ mesenchymal stem cells of the present invention may be greater than 45%, 50%, 55%, 60%, 65%, 70%, 75%, 80%, 85%, 90%, or 95%, CD107a$^{high}$ mesenchymal stem cells, derived from culture, may comprise CD45+CD31-, and differentiate into adipogenic cells under adipogenic differentiation conditions.

Another embodiment of the present invention is a population of cells comprising CD107a$^{high}$ adipogenic cells. A population of CD107a$^{high}$ adipogenic cells of the present invention may be greater than 45%, 50%, 55%, 60%, 65%, 70%, 75%, 80%, 85%, 90%, or 95%, CD107a adipogenic cells.

Another embodiment of the present invention is a population of cells comprising CD107a$^{low}$ mesenchymal stem cells. As stated above, a population of CD107a$^{low}$ mesenchymal stem cells of the present invention may be greater than 45%, 50%, 55%, 60%, 65%, 70%, 75%, 80%, 85%, 90%, or 95% CD107a$^{low}$ mesenchymal stem cells, derived from culture, may comprise CD45+CD31-, and differentiate into osteogenic cells under osteogenic differentiation conditions.

Another embodiment of the present invention is a population of cells comprising CD107a$^{low}$ osteogenic cells. A population of CD107a$^{low}$ osteogenic cells of the present invention may be greater than 45%, 50%, 55%, 60%, 65%, 70%, 75%, 80%, 85%, 90%, or 95% CD107a$^{low}$ osteogenic cells.

Another embodiment of the present invention is a method of treating or preventing a tissue defect in a subject comprising the steps of: providing CD107a$^{high}$ mesenchymal stem cells, with or without differentiating the CD107a$^{high}$ mesenchymal stem cells into CD107a$^{high}$ adipogenic cells; administering the CD107a$^{high}$ mesenchymal stem cells or CD107a$^{high}$ adipogenic cells to a subject having a tissue defect; and treating or preventing the tissue defect in the subject. The tissue defect is treated or prevented in the subject when compared to a reference subject who has a tissue defect and who was not been administered CD107a$^{high}$ mesenchymal stem cells or adipogenic cells. Soft tissue defects treated or prevented by the methods of the present invention may result from trauma, oncologic resection, congenital etiologies, non-healing ulcers, muscle wasting diseases, fat wasting diseases, and/or cosmesis associated with aging. The CD107a$^{high}$ mesenchymal stem cells and CD107a$^{high}$ adipogenic cells of the present invention may be administered to a subject as part of a pharmaceutical composition. Treatment methods of the present invention may be autologous whereby the CD107a$^{high}$ mesenchymal stem cells or the CD107a$^{low}$ mesenchymal stem cells are obtained from the subject receiving a treatment.

Another embodiment of the present invention is a method of treating or preventing a bone defect in a subject comprising the steps of: providing CD107a$^{low}$ mesenchymal stem cells; with or without differentiating the mesenchymal stem cells into CD107a$^{low}$ osteogenic cells; administering the CD107a$^{low}$ mesenchymal stem cells or CD107a$^{low}$ osteogenic cells to a subject having a bone defect; and treating or preventing the bone defect in the subject. The bone defect is treated or prevented in the subject when compared to a reference subject who has a bone defect and has not been administered the CD107a$^{low}$ mesenchymal stem cells or CD107a$^{low}$ osteogenic cells. The CD107a$^{low}$ mesenchymal stem cells or CD107a$^{low}$ osteogenic cells of the present invention may be administered to a subject as part of a pharmaceutical composition. As mentioned above, treatment method of the present invention may be autologous.

Another embodiment of the present invention is a method of treating or preventing a tissue defect in a subject comprising the steps of: administering a pharmaceutical composition of uncultured CD107a$^{high}$ mesenchymal stem cells or cultured CD107a$^{high}$ adipogenic cells to a subject having a tissue defect, and treating or preventing the tissue defect in the subject. The CD107a$^{high}$ adipogenic cells may also be CD45-CD31-.

Another embodiment of the present invention is a method of treating or preventing bone defects in a subject comprising the steps of: administering a pharmaceutical composition of uncultured CD107a$^{low}$ mesenchymal stem cells or cultured CD107a$^{low}$ osteogenic cells to a subject having a bone defect, and treating or preventing the bone defect in the subject. The CD107a$^{low}$ osteogenic cells may also be CD45-CD31-.

Another embodiment of the present invention is a method of using CD107a$^{high}$/a$^{low}$ expression as a diagnostic or quality control measure for identifying adipose tissue specimens for the treatment of tissue defects of fat or bone, comprising the steps of: providing a adipose tissue sample from a subject; identifying the frequency of CD107a$^{high}$ mesenchymal cell percentage and the frequency of CD107a$^{low}$ mesenchymal cell percentage of the adipose tissue sample; and identifying an adipose tissue sample for treating a bone or soft tissue defect when the CD107a$^{low}$ or CD107a$^{high}$ cell percentage is greater than 35%, 45% or 50%, respectively.

Unless defined otherwise, all technical and scientific terms used herein have the meaning commonly understood by a person skilled in the art to which this invention belongs.

The following references provide one of skill with a general definition of many of the terms used in this invention: As used herein, the following terms have the meanings ascribed to them below, unless specified otherwise.

By "adipogenic differentiation conditions" is meant the addition of factors to "basal cell culture conditions" as defined below, with additions including insulin (0-20 ug/ml), dexamethasone (0-5 uM), methylxanthine (0-5 mM), and indomethacin (0-500 uM). PPARg agonists, such as Rosiglitazone may be added, or proprietary formulations may be substituted, such as Mesencult Adipogenic differentiation medium (human) (Stemcell, catalog #05412).

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

By "basal cell culture condition" is meant standard growth mediums such as (1) DMEM (Dulbecco's Modified Eagle Medium) with 10% fetal bovine serum (FBS) with or without antibiotics, (2) EGM-2 (Endothelial Cell Growth Medium) (Lonza, Cat. #: CC-3162), or (3) a combination in various ratios of mediums 1 and 2. Similar growth mediums for mammalian cell culture may be substituted. FBS concentrations may vary from 0-25%.

By CD107a is meant Lysosomal-associated membrane protein 1 (LAMP-1) also known as lysosome-associated membrane glycoprotein 1 and CD107a (Cluster of Differentiation 107a), is a protein that in humans is encoded by the LAMP1 gene. The human LAMP gene is located on the long arm (q) of chromosome 13 at region 3, band 4 (13q34). CD107a or CD107a$^{high}$ means a cell is expressing the LAMP1 protein on the cell surface. CD107a$^{low}$ means a cell is not expressing the LAMP1 protein on the cell surface.

By "disease" is meant any condition, or disorder, that damage or interferes with the normal function of a cell, tissue, or organ. Examples of disease includes surgery that disrupts tissue morphology or disease or injury that damages bones.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "osteogenic differentiation conditions" is meant the addition of factors to "basal cell culture conditions" as defined above, with additions including 50 µg/ml Ascorbic Acid (range 0-200 ug/ml), and 10 mM R glycerophosphate (range 0-50 mM). Dexamathesone may or may not be included. Similar osteogenic differentiation mediums for mammalian cell culture may be substituted.

The term "reference" refers to a standard or control conditions such as a subject substantially free of a CD107a (lysosome-associated membrane protein-1) or CD107a$^{low}$ population of cells of the present invention.

By "reduces" is meant a negative alteration of at least 10%, 25%, 50%, 75%, or 100%.

By "subject" is meant any individual or patient to which the method described herein is performed. Generally, the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 1: Summary of frequency data for CD107a$^{high}$ mesenchymal cells (CD107a$^{high}$CD31$^-$CD45$^-$) cell frequency as well as CD107a$^{low}$ mesenchymal cell frequency (CD107a$^{low}$CD31$^-$CD45$^-$) as expressed as a percentage of total cells within the stromal vascular fraction of human adipose tissue. Data from six samples are summarized.

FIG. 3: BD FACSDiva Software representation of cell derivation of a CD107a$^{low}$CD31$^-$ CD45$^-$ mesenchymal cell population (right hand side, DN) and a CD107a$^{high}$CD31$^-$CD45$^-$ mesenchymal cell population (left hand side, CD107$^{high}$).

FIG. 4: Moflo Software representation of cell derivation of a CD107a$^{low}$CD31$^-$CD45$^-$ mesenchymal cell population (bottom left hand side, R5) and a CD107a$^{high}$CD31$^-$CD45$^-$ mesenchymal cell population (bottom left hand side, R6).

FIG. 5: Moflo Software representation of cell derivation of a CD107a$^{low}$CD31$^-$CD45$^-$ mesenchymal cell population (bottom left hand side) and a CD107a$^{high}$CD31$^-$CD45$^-$ mesenchymal cell population (bottom left hand side, R4).

FIG. 10: CD107a (LAMP-1) negative stromal cells are osteoprogenitors in human fat tissue. $CD107a^{low}$ and $CD107a^{high}$ mesenchymal cells from human adipose tissue were subject to osteogenic differentiation conditions over seven days. $CD107a^{low}$ cells demonstrated enhanced bone nodule deposition, visualized by Alizarin red S staining above and quantified by leaching and photometric quantification below.

FIG. 11: CD107a (LAMP-1) negative stromal cells are osteoprogenitors in human fat tissue. $CD107a^{low}$ and $CD107a^{high}$ mesenchymal cells from human adipose tissue were subject to osteogenic differentiation conditions over seven days. $CD107a^{low}$ cells demonstrated enhanced bone nodule deposition, visualized by Alizarin red S staining above and quantified by leaching and photometric quantification below.

FIG. 12: CD107a (LAMP-1) negative stromal cells are osteoprogenitors in human fat tissue. $CD107a^{low}$ and $CD107a^{high}$ mesenchymal cells from human adipose tissue were subject to osteogenic differentiation conditions over seven days. $CD107a^{low}$ cells demonstrated enhanced bone nodule deposition, visualized by Alizarin red S staining above and quantified by leaching and photometric quantification below.

FIG. 14: CD107a (LAMP-1) positive stromal cells are adipoprogenitors in human fat tissue. FACS identified $CD107a^{high}$ and $CD107a^{low}$ mesenchymal stromal cells from human white adipose tissue were subject to adipogenic differentiation conditions over seven days. Oil red O staining of lipid droplets (left) and photometric quantification at 10 days (right) among $CD107a^{high}$ and $CD107a^{low}$ cell subsets.

FIG. 15: CD107a (LAMP-1) positive stromal cells are adipoprogenitors in human fat tissue. FACS identified $CD107a^{high}$ and $CD107a^{low}$ mesenchymal stromal cells from human white adipose tissue were subject to adipogenic differentiation conditions over seven days. Oil red O staining of lipid droplets (left) and photometric quantification at 10 days (right) among $CD107a^{high}$ and $CD107a^{low}$ cell subsets.

FIG. 16: CD107a (LAMP-1) positive stromal cells are adipoprogenitors in human fat tissue. FACS identified $CD107a^{high}$ and $CD107a^{low}$ mesenchymal stromal cells from human white adipose tissue were subject to adipogenic differentiation conditions over seven days. Oil red O staining of lipid droplets (left) and photometric quantification at 10 days (right) among $CD107a^{high}$ and $CD107a^{low}$ cell subsets.

DETAILED DESCRIPTION OF THE INVENTION

CD107a (lysosome-associated membrane protein-1) is a member of a family of structurally related type 1 membrane proteins predominantly expressed in lysosomes and other intracellular vesicles. CD107a is also expressed on the cell surface, which is the result of both trafficking of nascent protein to the plasma membrane as well as the fusion of late endosomes and lysosomes to the cell membrane. In inflammatory cells, cell surface CD107a reflects the state of activation of cells and has been implicated in cell adhesion. To the best of the inventors' knowledge, CD107a has never been studied in the context of MSC biology, nor in bone- or fat-forming cells.

Figure 7:
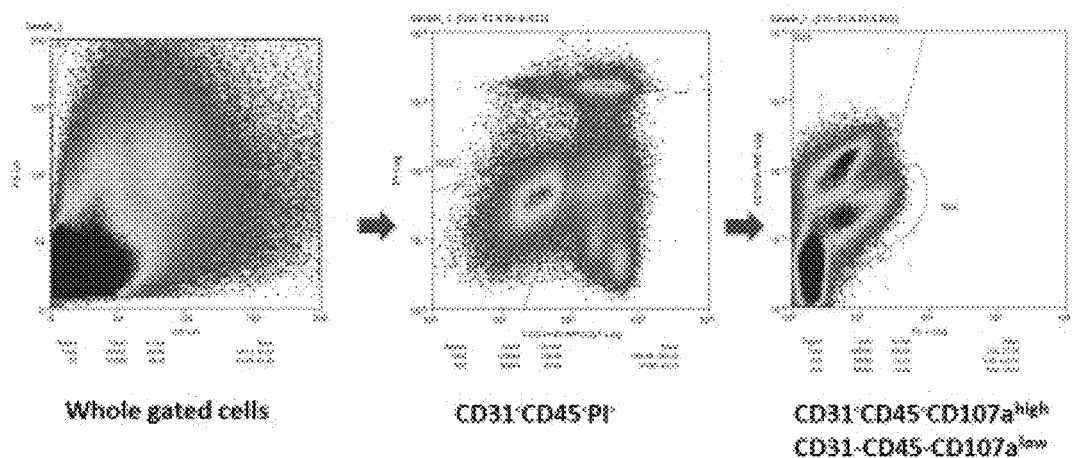
FIG. 7: Moflo Software representation of cell derivation of a CD107a$^{low}$CD31$^-$CD45$^-$ mesenchymal cell population (right hand side, R24) and a CD107a$^{high}$CD31$^-$CD45$^-$ mesenchymal cell population (bottom left hand side, R23).
Figure 8:
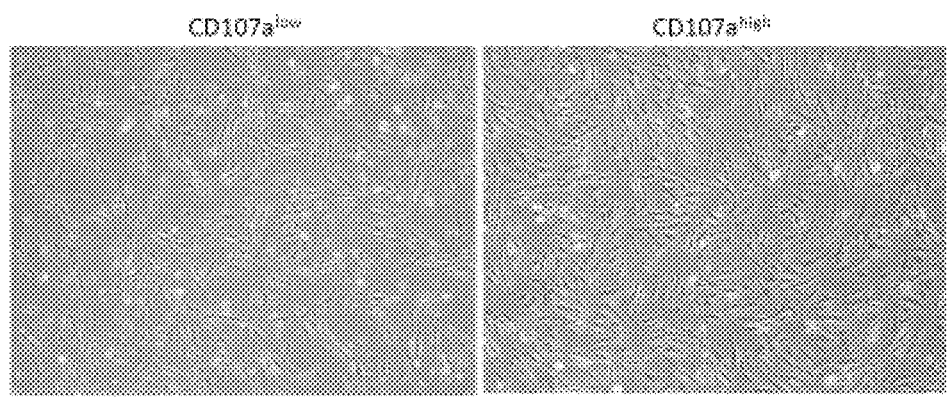
FIG. 8: Light microscopy appearance of freshly sorted CD107a$^{low}$ and CD107a$^{high}$ mesenchymal cells. Fibroblastic cell types are seen, and no distinguishable differences are observed among either purified cell type.

The present invention identified that CD107a is expressed in perivascular tissue locations within human adipose tissue. Cell surface CD107a can be used to purify subpopulations of human tissue adipose stroma (FIGS. 1-7, $CD107a^{high}CD31^-CD45^-$ represent on average 14.7% of total SVF), and may be used in analogous approaches from other mesenchymal tissues. Once isolated under basal cell culture conditions [DMEM (Dulbecco's Modified Eagle Medium) with 10% fetal bovine serum (FBS)] no morphologic differences are present between $CD107a^{high}$ and $CD107a^{low}$ stromal progenitors from human adipose (FIG. 8).

Figure 9:
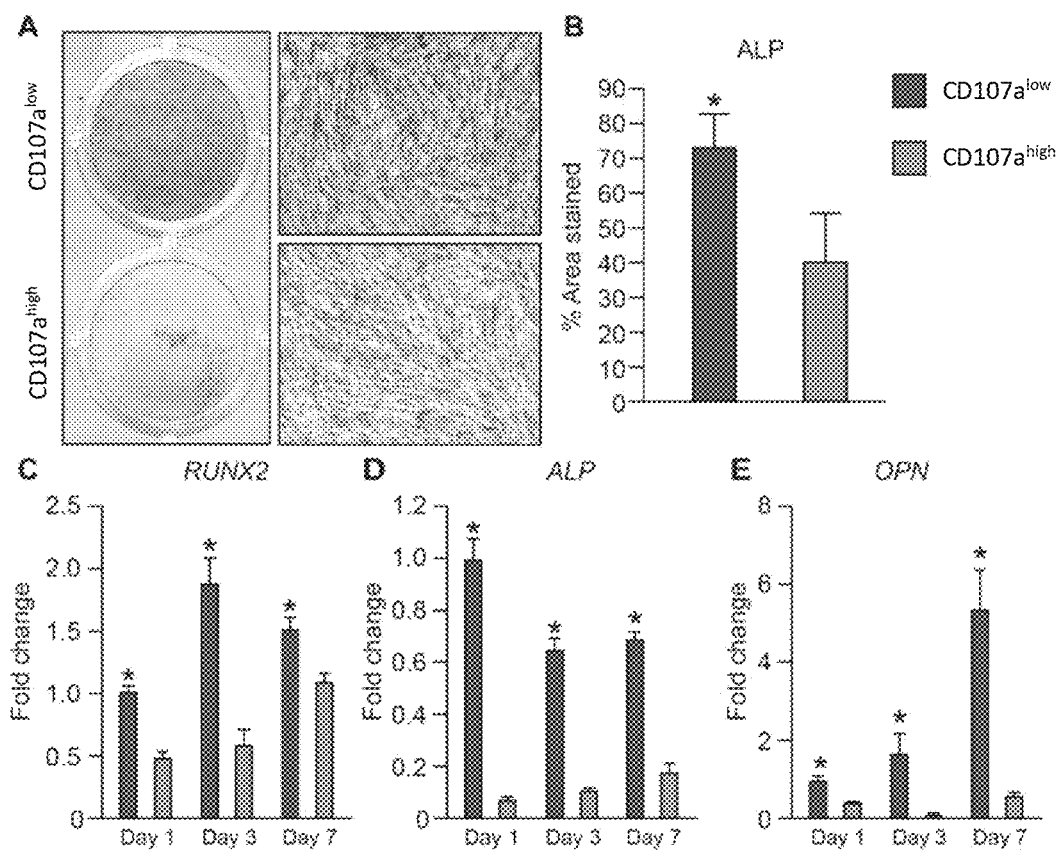
FIG. 9: CD107a (LAMP-1) negative stromal cells are osteoprogenitors in human fat tissue. FACS identified CD107a$^{high}$ and CD107a$^{low}$ mesenchymal stromal cells from human white adipose tissue were subject to osteogenic differentiation conditions over seven days. CD107a$^{low}$ cells demonstrated enhanced osteogenic differentiation across all markers. (A) Alkaline phosphatase staining (whole well and 20× magnification) and (B) photographic quantification at 7 days. (C) Specific gene expression assessed by qRT-PCR, including (C) RUNX2 (Runt related transcription factor 2), (D) ALP (Alkaline Phosphatase), and (E) OPN (Osteopontin) at 1, 3 and 7 days osteogenic differentiation. Performed in at least triplicate. *P<0.05.

In contrast, the differentiation potential of $CD107a^{high}$ and $CD107a^{low}$ subsets was starkly dissimilar (FIGS. 9-16). The inventors propagated CD107a subsets under standardized osteogenic differentiation conditions [DMEM (Dulbecco's Modified Eagle Medium) with 10% fetal bovine serum (FBS), 50 μg/ml Ascorbic Acid, and 10 mM β glycerophosphate] (FIG. 9-). Results showed that $CD107a^{low}$ progenitor cells had a strong predilection for osteogenic differentiation, including increased alkaline phosphatase enzymatic activity (FIG. 9A, B). The $CD107a^{low}$ also had increased bone nodule deposition (FIG. 10-12), and increased osteoblast specific gene expression across a sequential time course of osteodifferentiation (FIG. 9C-E).

Next, CD107a subsets were propagated under adipogenic differentiation conditions [Mesencult Adipogenic differentiation medium (human) (Stemcell, catalog #05412)]. Strikingly and unlike their $CD107a^{low}$ counterpart, results showed that $CD107a^{high}$ progenitor cells were highly primed for adipogenesis. This included Oil red O staining of lipid droplets and photometric quantification (FIG. 13-16), as well as adipocyte specific gene expression across sequential time points of adipogenic differentiation as assessed by qRT-PCR (FIG. 13C-F). Thus, cell surface CD107a expression separates adult, adipose-resident MSC into two populations with either a preference for bone or fat formation.

Figure 17:
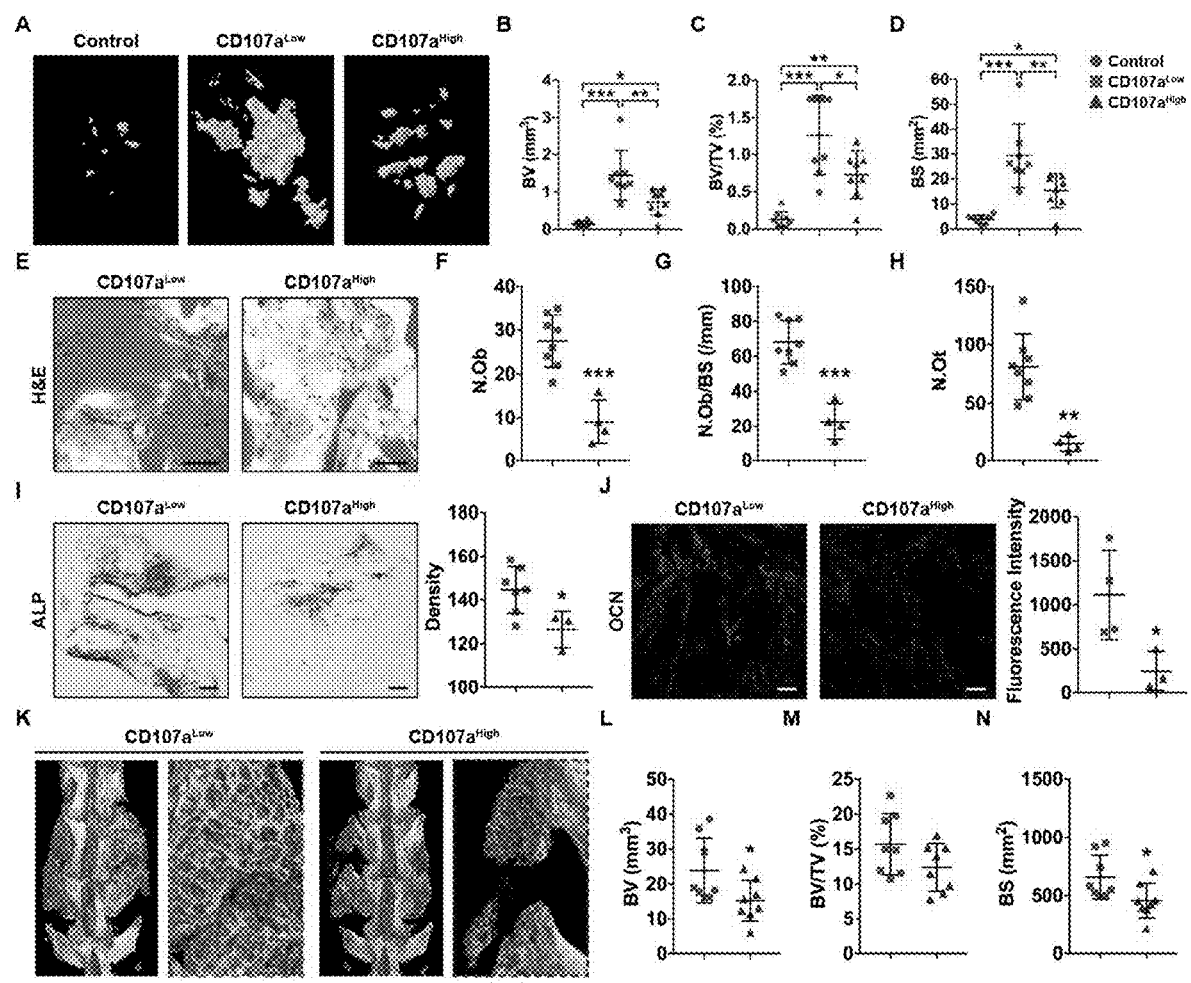
FIG. 17A-17N: $CD107a^{low}$ stromal cells promote bone regeneration in vivo. (A-J) FACS identified $CD107a^{high}$ and $CD107a^{low}$ mesenchymal stromal cells from human white adipose tissue were implanted intramuscularly using a DBM carrier. Bone formation was assayed after 8 weeks. (A) Representative microcomputed tomography reconstruction images of the implant site among control (DBM only), $CD107a^{low}$, and $CD107a^{high}$ mesenchymal stromal cells. (B) Mean bone volume (BV) among each treatment group. (C) Bone volume fraction (BV/TV). (D) Mean bone surface (BS). (E) Representative histologic appearance by routine H&E of $CD107a^{low}$ and $CD107a^{high}$ mesenchymal stromal cell implants. Black scale bar: 50 m. (F-H) Bone histomorphometric measurements among each treatment group, including (F) osteoblast number (N.Ob), (G) osteoblast number per bone surface (N.Ob/BS), and (H) osteocyte number (N.Ot). (I) Representative alkaline phosphatase (ALP) staining and quantification. Black scale bar: 50 μm. (J) Osteocalcin (OCN) immunohistochemistry, appearing red, with DAPI nuclear counterstain, appearing blue. Quantification of OCN activity in the implants was shown. White scale bar: 50 m. (K) Representative microcomputed tomography reconstruction images of the spine fusion site among $CD107a^{low}$ and $CD107a^{high}$ mesenchymal stromal cells. (L) Mean bone volume (BV) among each treatment group. (M) Bone volume fraction (BV/TV). (N) Mean bone surface (BS).

Having found that CD107a$^{low}$ adipose resident cells preferentially represented an osteoblast precursor, we next sought to extend that to in vivo transplantation studies (FIG. 17), including an intramuscular transplantation model and rat posterolateral lumbar spine fusion model. First, CD107a$^{low}$ and CD107a$^{high}$ cells subsets were derived from the same patient sample and mixed mechanically with a demineralized based bone matrix putty carrier (DBX Putty, MTF Biologics) before intramuscular implantation in NOD-SCID mice (FIG. 17A-J). DBX carrier without cells was used as a control. Intramuscular implants were imaged by micro computed tomography (μCT) at 8 weeks, demonstrating an accumulation of bone tissue among CD107a$^{low}$ laden implants in relation to either CD107a$^{high}$ implants or acellular control (FIG. 17A). Quantitative μCT analysis demonstrated a significant increase in bone volume (BV), fractional bone volume (BV/TV), and bone surfaces (BS) among CD107a$^{low}$ as compared to CD107a$^{high}$ implants (FIG. 17B-D). Histologic analysis revealed conspicuous areas of woven bone among CD107a$^{low}$ laden implants, which were not commonly seen among CD107a$^{high}$ implants (FIG. 17E). Bone histomorphometric analysis confirmed these observations, demonstrating significantly increased osteoblast number (N.Ob), increased osteoblast numbers per bone surface (N.Ob/BS), and osteocyte numbers (N.Ot) (FIG. 17F-H). ALP staining and semi-quantitative analysis confirmed an overall increase in serial sections of CD107a$^{low}$ treated implants (FIG. 17I). Enrichment in the terminal osteogenic differentiation marker Osteocalcin (OCN) was also confirmed among CD107a$^{low}$ implants, shown by immunostaining and semi-quantitative analysis (FIG. 17J).

Having observed that CD107a$^{low}$ cell preparations demonstrated enhanced ectopic bone formation, we next challenged these cells to a more challenging lumbar spine fusion model within athymic rats (FIG. 17K-N). CD107a$^{low}$ and CD107a$^{high}$ cells subsets from patient-identical samples on the DBX putty carrier were implanted bilaterally in an L4-L5 spine fusion model. Imaging studies were performed using μCT. μCT imaging and reconstructions demonstrated persistent radiolucency within the spinal fusion segments of CD107a$^{high}$ treated implant sites (FIG. 17K). Quantitative μCT analysis demonstrated a significant increase in BV and BS among CD107a$^{low}$ as compared to CD107a$^{high}$ implants (FIG. 17L-N). In summary, CD107a$^{low}$ stromal cell preparations demonstrate improvements in bone-forming potential across two orthopaedic models.

The inventors have overturned conventional thinking in the field by defining functionally relevant subpopulations of adipose derived MSC. The present invention represent a shift away from current thinking in the MSC field. Firstly, that a 'functional and developmental hierarchy' exists within adipose derived MSC. Previously conceptualized under the umbrella term 'Adipose derived stem cells,' the present invention suggests that the differentiation status of adipose MSC is both fluid and restricted. For example, on a clonal level ASC representative a mixture of multipotent, bipotent, and unipotent cell types. The inventors' discovery of cell surface markers that predict the level of MSC 'maturation' has led them to cell surface CD107a—a marker which is completely unstudied in MSC biology. The novel marker CD107a appears to be a crucial step in defining the functional and development hierarchy within the adipose niche and dictate a pro-osteogenic from pro-adipocytic population of human MSC. Not being held to any particular theory, the inventors believe a theoretical inverse relationship between osteogenic and adipogenic differentiation exists among multipotent progenitors and that CD107a expression will dictates this balance in two clinically relevant models of tissue engineering. Specifically the scientist believe that CD107a as a marker may dictate the balance between osteogenesis and adipogenesis in human MSC. The potential impact is broad, and includes both basic biologic and translational implications. The inventors' data on CD107a represent the first time that a cell surface marker has been shown to correlate to differentiation potential within MSC. In this regard, the study of CD107a within the stromal mesenchyme may represent a defining step toward understanding the broader 'developmental hierarchy' within MSC and adipose derived MSC. The present invention has improved the understanding of MSC subpopulations primed for either bone and fat formation has large scale implications for the stem cell field as applied to mesenchymal tissue engineering and regenerative medicine. MSC/progenitor cell therapies have high potential for the treatment a broad range of bone and soft tissue defects, whether from traumatic, surgical, or congenital etiologies. The present invention allows for better understanding of which MSC subpopulations are best used for bone or adipose tissue formation and is of immense value for future efforts in regenerative medicine.

Cell Populations

Adipose tissue (AT)-derived CD107a$^{high}$ and CD107a$^{low}$ progenitors have been purified as (described in the examples) and characterized. Human total stromal cells from adipose tissue (total CD45−CD31− mononuclear cells) or adventitial progenitor cells (APCs, CD34+CD146−C45−CD31− cells) were isolated from human lipoaspirate based on methods utilizing fluorescence-activated cell sorting (FACS). Feasibility of establishing viable and reliable cell populations of CD107a$^{high}$ and CD107a$^{low}$ total stroma or APCs was established by the present invention. For each sample, purity after FACS derivation was checked by both flow cytometry and PCR for endothelial (CD31, CD144), hematopoietic (CD45), and myogenic (CD56) markers. Demographics was recorded for each patient, including age, gender, and body mass index Embodiments of the disclosure concern methods and/or compositions for treating and/or preventing a tissue and/or bone defects in subjects. In certain embodiments, a subject with a soft tissue defect is administered with a population of CD107a$^{high}$ cells and a subject with a bone defect is administered with a population of CD107a$^{low}$ cells. The CD107a$^{high}$ cells may be differentiated into adipogenic cells and the CD107a$^{low}$ cells may be differentiated into osteogenic cells prior to administration to the subject. The CD107a$^{high}$ or CD107a$^{low}$ cells may alternatively be applied to a subject immediately after sorting and without pre-differentiation. The CD107a and CD107a$^{low}$ cells may be derived from the subject receiving the cells resulting in an autologous treatment.

An individual known to have a tissue defect or a bone defect, suspected of having a tissue defect or a bone defect, or at risk for having a tissue defect or a bone defect may be provided an effective amount of CD107a$^{high}$ or CD107a$^{low}$ cells, including CD107a$^{high}$ cells differentiated into adipogenic cells and/or CD107a$^{low}$ cells differentiated into osteogenic cells. Those at risk for a bone defect or tissue defect may be those individuals having one or more genetic factors, may be of advancing age, and/or may have a family history, for example.

In particular, embodiments of the disclosure, a subject is given an agent for treating a bone defect or tissue defect in addition to the one or more CD107a$^{high}$ or CD107a$^{low}$ cells. Such additional therapy may include in the case of bone defects recombinant BMP2, autologous bone marrow, allogeneic bone matrix, or related entities. Such additional therapy may include in the case of soft tissue defects, synthetic or biologic fillers. The additional therapy may be given prior to, at the same time as, and/or subsequent to the CD107a$^{high}$ or CD107a$^{low}$ cell therapy.

Pharmaceutical Preparations

Pharmaceutical compositions of the present invention comprise an effective amount of one or more CD107a and/or CD107a$^{low}$ cells such as CD107a cells differentiated into adipogenic cells and the CD107a$^{low}$ cells differentiated into osteogenic cells. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises one or more CD107a cells and/or CD107a$^{low}$ cells. The pharmaceutical composition may comprise an additional active ingredient known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The one or more CD107a and/or CD107a$^{low}$ cells may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The one or more CD107a and/or CD107a$^{low}$ cells may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art. In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more CD107a and/or CD107a$^{low}$ cells, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the one or more CD107a and/or CD107a$^{low}$ cells may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose of CD107a$^{low}$ cells for bone defect administration may also comprise from about $1\times10^4$, about $1\times10^5$ cells per mL, about $1\times10^6$ cells per mL, about $1\times10^7$ cells per mL, about $1\times10^8$ cells per mL, or about $1\times10^9$ cells per mL or more per administration, and any range derivable therein. In other non-limiting examples, a dose of CD107a$^{high}$ cells for soft defect augmentation may also comprise from about $1\times10^4$, about $1\times10$ cells per mL, about $1\times10^6$ cells per mL, about $1\times10^7$ cells per mL, about $1\times10^8$ cells per mL, or about $1\times10^9$ cells per mL or more per administration, and any range derivable therein.

METHODS/EXAMPLES

The following Examples/Methods have been included to provide guidance to one of ordinary skill in the art for practicing representative embodiments of the presently disclosed subject matter. In light of the present disclosure and the general level of skill in the art, those of skill can appreciate that the following Examples/Methods are intended to be exemplary only and that numerous changes, modifications, and alterations can be employed without departing from the scope of the presently disclosed subject matter. The following Examples/Methods are offered by way of illustration and not by way of limitation.

Isolation of CD107a$^{high}$/Ow Populations by Flow Cytometry

Solutions
    Digestion solution: DMEM+0.5% (v/v) BSA+1 mg/ml collagenase II-S
    Red blood cell (RBC) lysis buffer: 9 parts of stock 1 (see below) are added to 1 part of stock 2, and the pH adjusted to pH 7.65 with 1M hydrochloric acid
    Stock 1: 8.3 g ammonium chloride in 1 L dH$_2$O
    Stock 2: 20.59 g Tris base in 1 L dH$_2$O after adjusting pH to 7.65 with 1M HCl
    Flow cytometry staining buffer: PBS/2% FBS (v/v)

Antibodies
    CD31 APC-cy7 (BD Biosciences, 1:100)
    CD45 APC-cy7 (BD Biosciences, 1:100)
    CD107a-BV421 (BD Biosciences, 1:100)

Methods

Combine approximately 150 ml adipose tissue with 100 ml PBS. Mix thoroughly by manually shaking the tubes for 30 s. Transfer 50 ml lipoaspirate/PBS mixture into 50 ml tubes. Centrifuge the tubes at 2000 rpm for 10 min at room temperature. Remove the oil from the top layer and transfer the fat into a new 50 ml tube. Mix approximately 25 ml tissue with 25 ml PBS/2% FBS (v/v) in 50 ml tubes. Centrifuge the tubes at 2000 rpm for 10 min at room temperature. Remove the supernatant and add 25 ml digestion solution (DMEM+0.5% (v/v) BSA+1 mg/ml collagenase II-S) to the remaining fat. Transfer the tubes to the shaking water bath at 37° C., 150 rpm, for 45 min. After incubation, centrifuge the tubes at 2000 rpm for 10 min at room temperature. Aspirate the supernatant (containing oily fat and adipocytes) and resuspend each pellet in pre-warmed 25 ml PBS/2% FBS (v/v). Pass the tissue suspension through the 400 μm Strainer to remove any persistent clumps or undigested material. Filter the tissue suspension sequentially through 100 μm and 70 μm cell strainers. Add PBS/2% FBS (v/v) to give 50 ml total and centrifuge at 2000 rpm for 10 min. Aspirate/discard the supernatant and resuspend the pellet(s) in 10 ml RBC lysis buffer. Incubate at room temperature for 5-10 min. Add 20 ml PBS/2% FBS (v/v) to the tube(s) and filter the resulting suspension through a 40 μm cell strainer. Top up the filtered solution with PBS/2% FBS (v/v) and centrifuge at 1500 rpm for 10 min. Aspirate/discard the supernatant and resuspend the pellet (comprised of the SVF) in 5-10 ml PBS/2% FBS (v/v) to count. Resuspend cells in PBS/2% FBS (v/v) for immunostaining at a cell density of $1\times10^7$ cells per ml Staining
1. Prepare 4 falcon tubes as outlined below:
    Tube 1: Unstained cells
    Tube 2: Fully Stained sample
    Tube 3: single color control for CD45/CD31
    Tube 4: single color control for CD107a
    Tube 5: single color control for PI (dead cells and debris)
2. Add 100 μl of cell suspension to Tubes 1, 3, 4
3. Add the rest of cell suspension to Tube 2.
4. Add antibodies as detailed below to give a final dilution of 1:100.
    Tube 1: no antibodies
    Tube 2: CD31, CD45, CD107a
    Tube 3: CD31, CD45
    Tube 4: CD107a
    Tube 5: PI (5 ul per 1 million sample with 200 ul buffer)

Gating Strategy

Adjust voltages using an unstained sample and check staining on a fully stained sample to make sure all signals are on scale. Check single colour compensation controls to ensure each single stain is brightest in its own channel then run automatic compensation. Gate on cell population excluding debris. Gate for single cells only using SSC to discriminate doublets. Exclude haematopoietic (CD45 positive) endothelial (CD31 positive) cells utilizing the APC-cy7 dump channel.

Cell Collection and Culture

Figure 2:
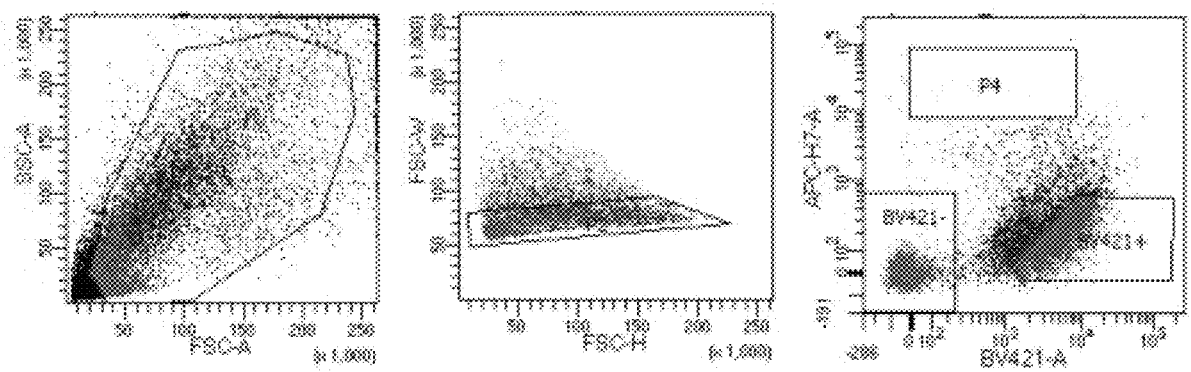
FIG. 2: BD FACSDiva Software representation of cell derivation of a CD107a$^{low}$CD31-CD45$^-$ mesenchymal cell population (right hand side, BV421$^-$) and a CD107a$^{high}$CD31$^-$CD45$^-$ mesenchymal cell population (right hand side, BV421$^+$).
Figure 6:
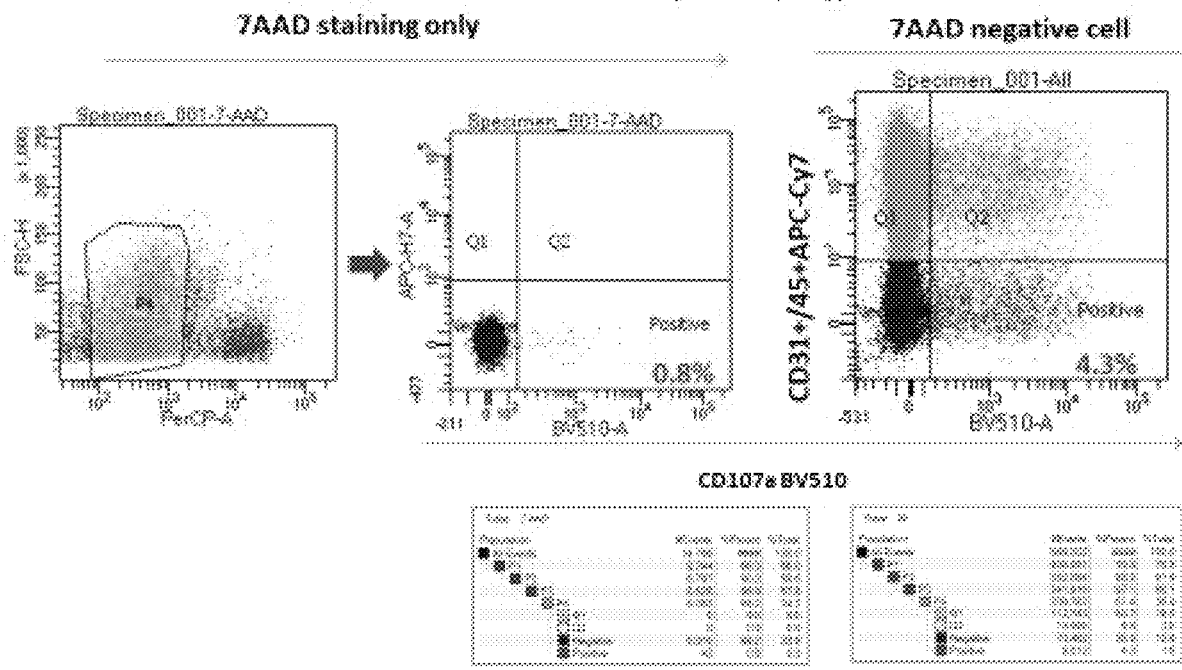
FIG. 6: BD FACSDiva Software representation of cell derivation of a CD107a$^{low}$CD31$^-$CD45$^-$ mesenchymal cell population (right hand side, Negative) and a CD107a$^{high}$CD31$^-$CD45$^-$ mesenchymal cell population (right hand side, Positive).
Figure 13:
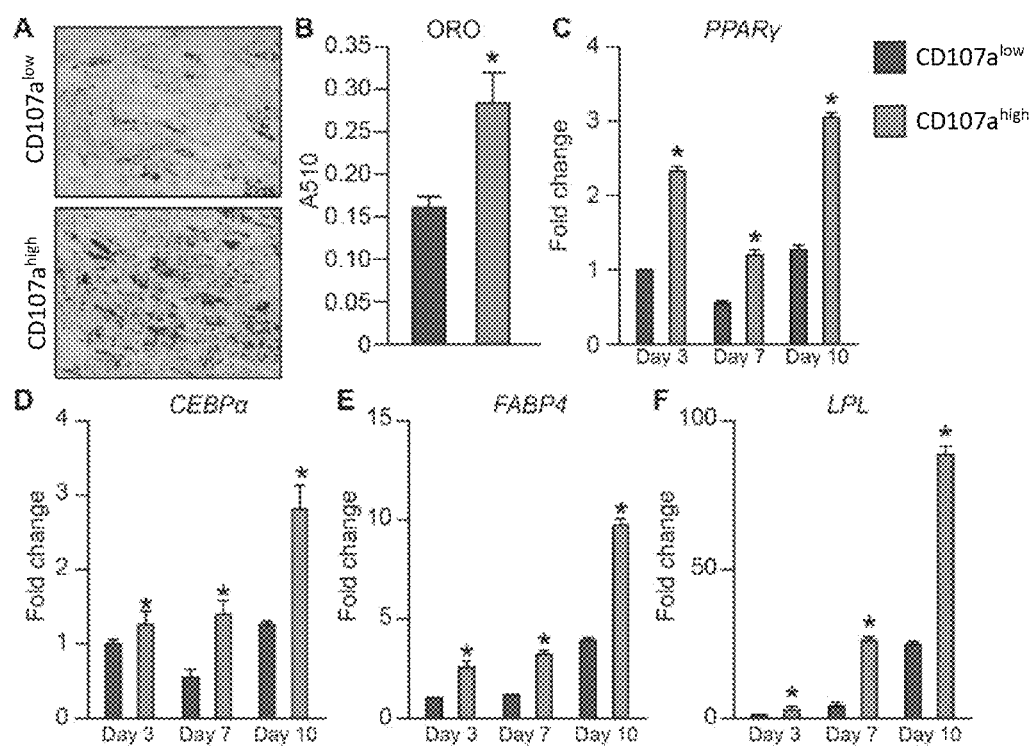
FIG. 13: CD107a (LAMP-1) positive stromal cells are adipoprogenitors in human fat tissue. FACS identified $CD107a^{high}$ and $CD107a^{low}$ stromal cells from human white adipose tissue were subject to adipogenic differentiation conditions over ten days. $CD107a^{high}$ cells demonstrated enhanced adipogenic differentiation across all markers. (A) Oil red O staining of lipid droplets (40× magnification) and (B) photometric quantification at 10 days. (C) Specific gene expression assessed by qRT-PCR, including (C) PPARG (Peroxisome proliferator-activated receptor gamma), (D) CEBPA (CCAAT/enhancer-binding protein-alpha), (E) FABP4 (fatty acid binding protein 4) and (F) LPL (lipoprotein lipase) at 3, 7 and 10 days adipogenic differentiation. Performed in at least triplicate. *$P<0.05$.

Collect $CD107a^{high}$ and $CD107a^{low}$ cells into 2 separate 5 ml polypropylene tubes containing EGM2 media. Following FACS collected cells are cultured on gelatin coated wells at a density of $2\times10^4$ cells per $cm^2$. Change EGM2 medium after 7 days, then every 3 days until 100% confluency is reached Figures were generated using the methods of the present invention, FIG. 1 provides a summary of frequency data for $CD107a^{high}$ mesenchymal cells ($CD107a^{high}CD31^-CD45^-$) cell frequency as well as $CD107a^{low}$ mesenchymal cell frequency ($CD107a^{low}CD31^-CD45^-$) as expressed as a percentage of total cells within the stromal vascular fraction of human adipose tissue. FIG. 2 provides BD FACSDiva Software representation of cell derivation of a $CD107a^{low}CD31^-CD45^-$ mesenchymal cell population (right hand side, $BV421^-$) and a $CD107a^{high}CD31^-CD45^-$ mesenchymal cell population (right hand side, $BV421^+$). FIG. 3 provides a BD FACSDiva Software representation of cell derivation of a $CD107a^{low}$ $CD31^-CD45^-$ mesenchymal cell population (right hand side, DN) and a $CD107a^{high}CD31^-CD45^-$ mesenchymal cell population (left hand side, $CD107a^{high}$). FIG. 4 provides a Moflo Software representation of cell derivation of a $CD107a^{low}CD31^-CD45^-$ mesenchymal cell population (bottom left hand side, R5) and a $CD107a^{high}CD31^-CD45^-$ mesenchymal cell population (bottom left hand side, R6). FIG. 5 provides a Moflo Software representation of cell derivation of a $CD107a^{low}CD31^-CD45^-$ mesenchymal cell population (bottom left hand side) and a $CD107a^{high}CD31^-CD45^-$ mesenchymal cell population (bottom left hand side, R4). FIG. 6 provides a BD FACSDiva Software representation of cell derivation of a $CD107a^{low}$ $CD31^-CD45^-$ mesenchymal cell population (right hand side, Negative) and a $CD107a^{high}CD31^-CD45^-$ mesenchymal cell population (right hand side, Positive). FIG. 7 provides a Moflo Software representation of cell derivation of a $CD107a^{low}$ $CD31^-CD45^-$ mesenchymal cell population (right hand side, R24) and a $CD107a^{high}CD31^-CD45^-$ mesenchymal cell population (bottom left hand side, R23). FIG. 8 provides a light microscopy appearance of freshly sorted $CD107a^{low}$ and $CD107a^{high}$ mesenchymal cells. Fibroblastic cell types were observed, and no distinguishable differences were observed among either purified cell type. FIG. 9 provides a CD107a (LAMP-1) negative stromal cells were osteoprogenitors in human fat tissue. FACS identified $CD107a^{high}$ and $CD107a^{low}$ mesenchymal stromal cells from human white adipose tissue were subject to osteogenic differentiation conditions over seven days. $CD107a^{low}$ cells demonstrated enhanced osteogenic differentiation across all markers. FIG. 10 illustrates that CD107a (LAMP-1) negative stromal cells were osteoprogenitors in human fat tissue. $CD107a^{low}$ and $CD107a^{high}$ mesenchymal cells from human adipose tissue were subject to osteogenic differentiation conditions over seven days. $CD107a^{low}$ cells demonstrated enhanced bone nodule deposition, visualized by Alizarin red S staining above and quantified by leaching and photometric quantification below. FIG. 11 illustrates CD107a (LAMP-1) negative stromal cells were osteoprogenitors in human fat tissue. $CD107a^{low}$ and $CD107a^{high}$ mesenchymal cells from human adipose tissue were subject to osteogenic differentiation conditions over seven days. $CD107a^{low}$ cells demonstrated enhanced bone nodule deposition, visualized by Alizarin red S staining above and quantified by leaching and photometric quantification below. FIG. 12 illustrates CD107a (LAMP-1) negative stromal cells were osteoprogenitors in human fat tissue. $CD107a^{low}$ and $CD107a^{high}$ mesenchymal cells from human adipose tissue were subject to osteogenic differentiation conditions over seven days. $CD107a^{low}$ cells demonstrated enhanced bone nodule deposition, visualized by Alizarin red S staining above and quantified by leaching and photometric quantification below. FIG. 13 illustrates that CD107a (LAMP-1) positive stromal cells were adipoprogenitors in human fat tissue. FACS identified $CD107a^{high}$ and $CD107a^{low}$ stromal cells from human white adipose tissue were subject to adipogenic differentiation conditions over ten days. $CD107a^{high}$ cells demonstrated enhanced adipogenic differentiation across all markers. FIG. 14 illustrates CD107a (LAMP-1) positive stromal cells were adipoprogenitors in human fat tissue. FACS identified $CD107a^{high}$ and $CD107a^{low}$ mesenchymal stromal cells from human white adipose tissue were subject to adipogenic differentiation conditions over seven days. FIG. 15 illustrates CD107a (LAMP-1) positive stromal cells were adipoprogenitors in human fat tissue. FACS identified $CD107a^{high}$ and $CD107a^{low}$ mesenchymal stromal cells from human white adipose tissue were subject to adipogenic differentiation conditions over seven days. FIG. 16 illustrates CD107a (LAMP-1) positive stromal cells were adipoprogenitors in human fat tissue. FACS identified $CD107a^{high}$ and $CD107a^{low}$ mesenchymal stromal cells from human white adipose tissue were subject to adipogenic differentiation conditions over seven days.

Osteogenic Differentiation

For RNA isolation, $CD107a^{high}$ cells were seeded in six-well plates at a density of $1\times10^5$ cells per well and allowed to adhere overnight. Cells were cultured in osteogenic differentiation medium (ODM) constituted with 10 mM β-glycerophosphate and 50 μM ascorbic acid in DMEM+20% FBS. ODM was changed every third day for up to 14 days, until RNA isolation or staining was performed.

Alkaline phosphatase (ALP) staining was performed using the leukocyte alkaline phosphatase kit (Sigma-Aldrich). For ALP staining, cells were seeded in 24-well plates at a density of $3\times10^4$ cells/well. Cells were cultured under osteogenic differentiation conditions for 14 days before staining. Cells were then washed with PBS and fixed with formalin for 10 min at room temperature. Following fixation, cells were stained using the leukocyte alkaline phosphatase kit (Sigma-Aldrich) according to the manufacturer's protocol. Cells were incubated in ALP stain for 30 min at room temperature and then washed with PBS. Cells were allowed to dry and pictures were taken at 40% magnification using the Leica ICC50W inverted microscope (Leica Microsystems, Buffalo Grove, IL). Relative staining w % as quantified using Adobe Photoshop CC.

Adipogenic Differentiation

For RNA isolation, $CD107a^{high/low}$ cells were seeded in six-well plates at a density of $1\times10^5$ cells per well and allowed to adhere overnight. Medium was then replaced with the MesenCult adipogenic differentiation medium (StemCell Technologies, Inc., Vancouver, BC). Cells were cultured under adipogenic differentiation conditions for up to 10 days for gene expression analysis. Differentiation medium was changed every 3 days.

For oil red O (CRO) staining, cells were seeded in 24-well plates at a density of $3\times10^4$ cells/well and allowed to adhere overnight. Medium was then replaced with the MesenCult adipogenic differentiation medium (StemCell Technologies, Inc., Vancouver, BC). For visualization ORO staining, after 10 days of adipogenic differentiation, cells were washed with PBS and fixed with 10% formalin for 30 min. ORO stock solution was prepared from powder (Sigma, St. Louis, MO) by mixing 300 mg ORO powder with 100 mL of 99% isopropanol. Stock solution was diluted 3:2 stock solution: deionized water and allowed to sit at room temperature for 10 min. The working solution was then filtered by gravity filtration. After fixation by formalin, cells were washed with water and 60% isopropanol was added to wells for 5 min before staining. ORO working solution was then added to each well and incubated at 37° C. for 30 min. Following incubation, the cells were washed with tap water and counterstained with hematoxylin for 1 min. Images were taken using the Leica ICC50W inverted microscope (Leica Microsystems, Buffalo Grove, IL).

Ribonucleic Acid and Quantitative Real-Time Polymerase Chain Reaction

Gene expression was assayed by quantitative real-time polymerase chain reaction (qRT-PCR). Cells were seeded in 6-well plates at a density of $1\times10^5$ cells/Well and cultured in either adipogenic or osteogenic medium for up to 14 days. Time points for specific gene expression include 3, 7, and 10 days for the analysis of adipogenic (PPARγ, CEBPa, FABP4, and LPL) and 1, 3, and 7 days for the analysis of osteogenic markers (RUNX2, ALP, OPN). Briefly, total RNA was extracted using the RNeasy Kit (Qiagen, Santa Clarita, CA). One microgram of total RNA from each sample was then subjected to first-strand complementary deoxyribonucleic acid (cDNA) synthesis using the iScript cDNA synthesis kit (Bio-Rad, Hercules, CA) to a final volume of 20 μL. The reverse transcription reaction was performed at 25° C. for 5 minutes, 46° C. for 20 minutes, and 95° C. for 1 minute. Quantitative real-time polymerase chain reaction (qRT-PCR) reactions were run using the CFX96 Real-Time PCR detection system (Bio-Rad). Reactions were incubated in 96-well optical plates at 95° C. for 10 minutes, followed by 40 cycles at 95° C. for 15 s, and at 60° C. for 60 s. The threshold cycle (Ct) data were determined using default threshold settings. The Ct was defined as the fractional cycle number at which the fluorescence passes the fixed threshold. Reactions were run in duplicate to triplicate per RNA isolate and compared to the housekeeping gene, β-Actin (ACTB). Table 1 list the primers used in the present invention.

TABLE 1

| Gene | Primers Forward | Reverse |
|---|---|---|
| ACTB | 5'-CTGGAACGG TGAAGGTGA CA-3' (SEQ ID NO: 1) | 5'-AAGGGACTT CCTGTAACA ATGCA-3' (SEQ ID NO: 11) |
| ALP | 5'-GACCCTTGA CCCCCACAA T-3' (SEQ ID NO: 2) | 5'-GCTCGTACT GCATGTCCC CT-3' (SEQ ID NO: 12) |
| CEBPα | 5'-TGGACAAGA ACAGCAACG AGTA-3' (SEQ ID NO: 3) | 5'-ATTGTCACT GGTCAGCTC CAG-3' (SEQ ID NO: 13) |
| COL1A1 | 5'-TACCCCACT CAGCCCAGT GT-3' (SEQ ID NO: 4) | 5'-ACCAGACAT GCCTCTTGT CCTT-3' (SEQ ID NO: 14) |
| FABP4 | 5'-ACGAGGA TGATAAACT GGTGG-3' (SEQ ID NO: 5) | 5'-GCGAACTTC AGTCCAGGT CAAC-3' (SEQ ID NO: 15) |
| LPL | 5'-TTGCAGAGA GAGGACTCG GA-3' (SEQ ID NO: 6) | 5'-GGAGTTGCA CCTGTATGC CT-3' (SEQ ID NO: 16) |
| OCN | 5'-ATGAGAGCC CTCACACTC CTC-3' (SEQ ID NO: 7) | 5'-GCCGTAGAA GCGCCGATA GGC-3' (SEQ ID NO: 17) |
| OPN | 5'-CCTCCTAGG CATCACCTG TG-3' (SEQ ID NO: 8) | 5'-CCACACTAT CACCTCGGC C-3' (SEQ ID NO: 18) |
| PPARγ | 5'-GGGGTGATG TGTTTGAAC TTG-3' (SEQ ID NO: 9) | 5'-GACAGGAAA GACAACAGA CAAATC-3' (SEQ ID NO: 19) |
| RUNX2 | 5'-ATGGCGGGT AACGATGAA AAT-3' (SEQ ID NO: 10) | 5'-ACGGCGGGG AAGACTGTG C-3' (SEQ ID NO: 20) |

Having found that $CD107a^{low}$ adipose resident cells preferentially represented an osteoblast precursor, we next sought to extend that to in vivo transplantation studies (FIG. 17), including an intramuscular transplantation model and rat posterolateral lumbar spine fusion model. First, $CD107a^{low}$ and C cells subsets were derived from the same patient sample and mixed mechanically with a demineralized based bone matrix putty carrier (DBX Putty, MTF Biologics) before intramuscular implantation in NOD-SCID mice (FIG. 17A-J). DBX carrier without cells was used as a control. Intramuscular implants were imaged by micro computed tomography (CT) at 8 weeks, demonstrating an accumulation of bone tissue among $CD107a^{low}$ laden implants in relation to either $CD107a^{high}$ implants or acellular control (FIG. 17A). Quantitative CT analysis demonstrated a significant increase in bone volume (BV), fractional bone volume (BV/TV), and bone surfaces (BS) among $CD107a^{low}$ as compared to $CD107a^{high}$ implants (FIG. 17B-D). Histologic analysis revealed conspicuous areas of woven bone among $CD107a^{low}$ laden implants, which were not commonly seen among $CD107a^{high}$ implants (FIG. 17E). Bone histomorphometric analysis confirmed these observations, demonstrating significantly increased osteoblast number (N.Ob), increased osteoblast numbers per bone surface (N.Ob/BS), and osteocyte numbers (N.Ot) (FIG. 17F-H). ALP staining and semi-quantitative analysis confirmed an overall increase in serial sections of CD107a$^{low}$ treated implants (FIG. 17I). Enrichment in the terminal osteogenic differentiation marker Osteocalcin (OCN) was also confirmed among CD107a$^{low}$ implants, shown by immunostaining and semi-quantitative analysis (FIG. 17J).

Having observed that CD107a$^{low}$ cell preparations demonstrated enhanced ectopic bone formation, we next challenged these cells to a more challenging lumbar spine fusion model within athymic rats (FIG. 17K-N). CD107a$^{low}$ and CD107a$^{high}$ cells subsets from patient-identical samples on the DBX putty carrier were implanted bilaterally in an L4-L5 spine fusion model. Imaging studies were performed using μCT. μCT imaging and reconstructions demonstrated persistent radiolucency within the spinal fusion segments of CD107a$^{high}$ treated implant sites (FIG. 17K). Quantitative μCT analysis demonstrated a significant increase in BV and BS among CD107a$^{low}$ as compared to CD107a$^{high}$ implants (FIG. 17L-N). In summary, CD107a$^{low}$ stromal cell preparations demonstrate improvements in bone-forming potential across two orthopaedic models.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A method of separating $CD107a^{high}$ mesenchymal cells from $CD107a^{low}$ mesenchymal stem cells comprising the steps of:
   providing mesenchymal stem cells from adipose tissue;
   mixing labeled anti-CD107a with the mesenchymal stem cells; and
   sorting the mesenchymal stem cells into a population of $CD107a^{high}$ mesenchymal stem cells and a population of $CD107a^{low}$ mesenchymal stem cells, wherein:
   (i) the $CD107a^{high}$ mesenchymal stem cells are $CD45^+$ $CD31^-$ and adipoprogenitors, and,
   ii the $CD107a^{low}$ mesenchymal stem cells are $CD45^+$ $CD31^-$ and osteogenic progenitors.

2. The method of claim 1 wherein the population of $CD107a^{high}$ mesenchymal stem cells and the population of $CD107a^{low}$ mesenchymal cells are undifferentiated cells.

3. The method of claim 2 wherein the undifferentiated cells are grown under basal cell culture conditions.

4. The method of claim 1 wherein the population of $CD107a^{high}$ mesenchymal stem cells is greater than 50% $CD107a^{high}$ mesenchymal stem cells.

5. The method of claim 1 wherein the population of $CD107a^{low}$ mesenchymal stem cells is greater than 50% $CD107a^{low}$ mesenchymal stem cells.

* * * * *